(12) United States Patent
Hasegawa

(10) Patent No.: US 10,893,739 B2
(45) Date of Patent: Jan. 19, 2021

(54) FACE MASK

(71) Applicant: AMG Co., Ltd., Tokyo (JP)

(72) Inventor: Hiroki Hasegawa, Tokyo (JP)

(73) Assignee: AMG CO., LTD., Tokyo (JP)

( * ) Notice: Subject to any disclaimer, the term of this patent is extended or adjusted under 35 U.S.C. 154(b) by 0 days.

(21) Appl. No.: 16/616,811

(22) PCT Filed: May 10, 2019

(86) PCT No.: PCT/JP2019/018827
§ 371 (c)(1),
(2) Date: Nov. 25, 2019

(87) PCT Pub. No.: WO2020/039662
PCT Pub. Date: Feb. 27, 2020

(65) Prior Publication Data
US 2020/0359769 A1 Nov. 19, 2020

(30) Foreign Application Priority Data

Aug. 22, 2018 (WO) .................. PCT/JP2018/031048

(51) Int. Cl.
*A45D 44/00* (2006.01)
(52) U.S. Cl.
CPC .................. *A45D 44/002* (2013.01)
(58) Field of Classification Search
CPC ........ A45D 44/002; A61M 2210/0606; A61M 35/10; A61K 8/0212; A61Q 19/00
See application file for complete search history.

(56) References Cited

U.S. PATENT DOCUMENTS

2009/0241242 A1* 10/2009 Beatty .................. A45D 44/002
2/206

FOREIGN PATENT DOCUMENTS

| JP | 3045353 U | 1/1998 | |
| JP | 2004-315539 A | 11/2004 | |
| JP | 3128445 U | 1/2007 | |
| JP | 2009-240788 A | 10/2009 | |
| JP | 4352416 B | 10/2009 | |
| JP | 4352416 B2 * | 10/2009 | ............. A45D 44/22 |
| JP | 2012-040250 A | 3/2012 | |
| JP | 2015-130900 A | 7/2015 | |
| WO | WO 2014/153687 A1 | 10/2014 | |
| WO | WO 2014/174595 A1 | 10/2014 | |

\* cited by examiner

*Primary Examiner* — Ophelia A Hawthorne
*Assistant Examiner* — Alessandro R Del Priore
(74) *Attorney, Agent, or Firm* — Muncy, Geissler, Olds & Lowe, P.C.

(57) ABSTRACT

A face mask for beauty treatment with a cosmetic composition in the user's face which has a convex and concave shape. The nose portion of the mask comes into contact with the user's nose, a plurality of adjustment structures formed independently of each other arranged in a portion on the left side of a center line and a portion on the right side thereof, respectively. Each adjustment structure is formed independently of a cut defining the external shape of the nose portion, and has a space boundary portion with two points separated in a direction different from a center line and forming a space through a cut connecting below or above the two points. A non-moving portion arranged in the space with the same shape as the space and at the location connecting the two points is connected to the main body of the face mask.

4 Claims, 15 Drawing Sheets

[Figure 1]
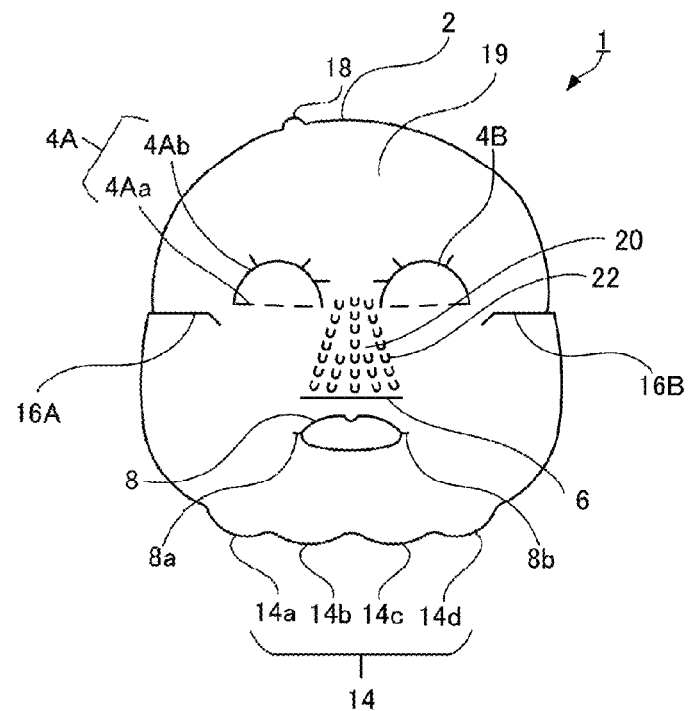
[Figure 2]
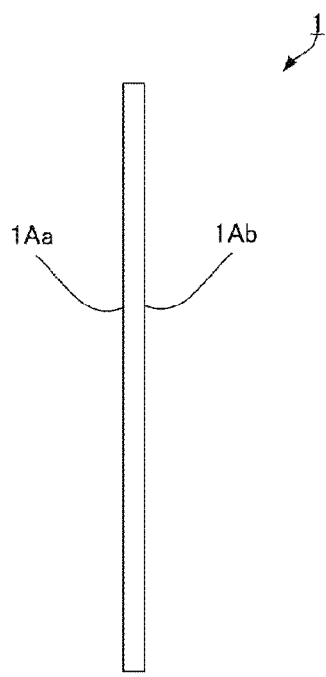

[Figure 3]
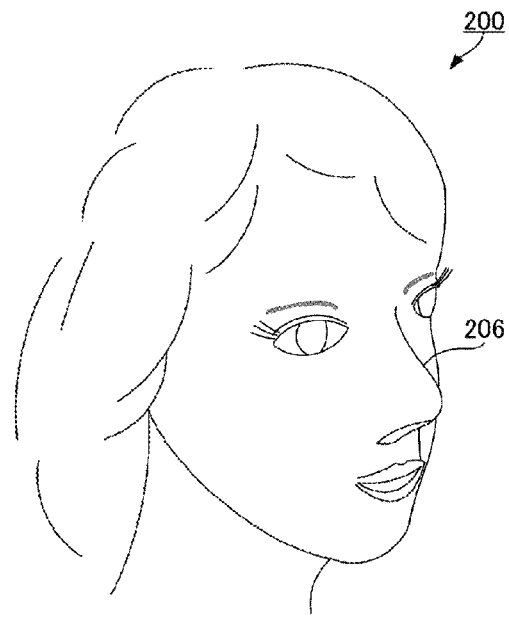
[Figure 4]
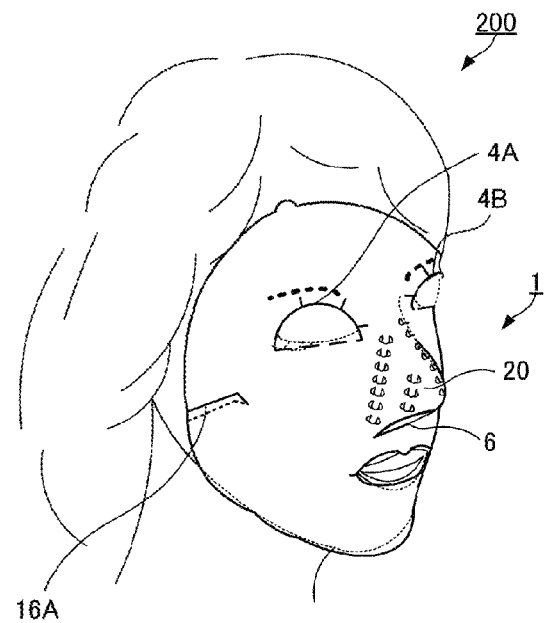

[Figure 5]
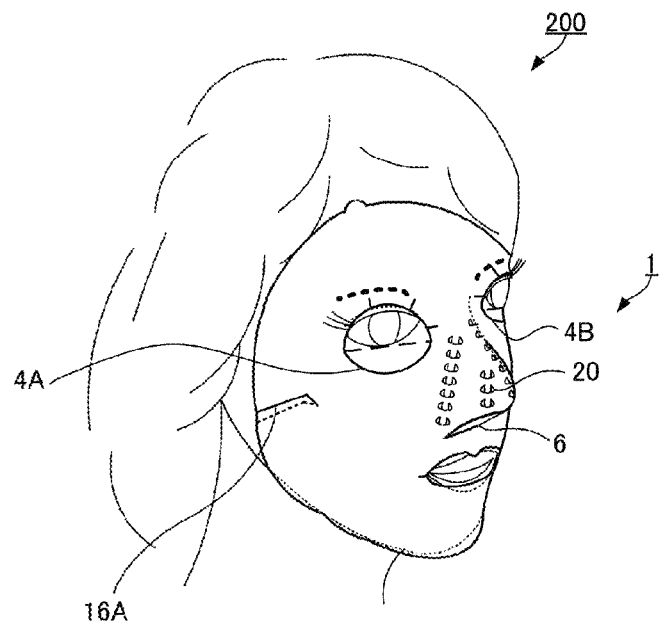
[Figure 6]
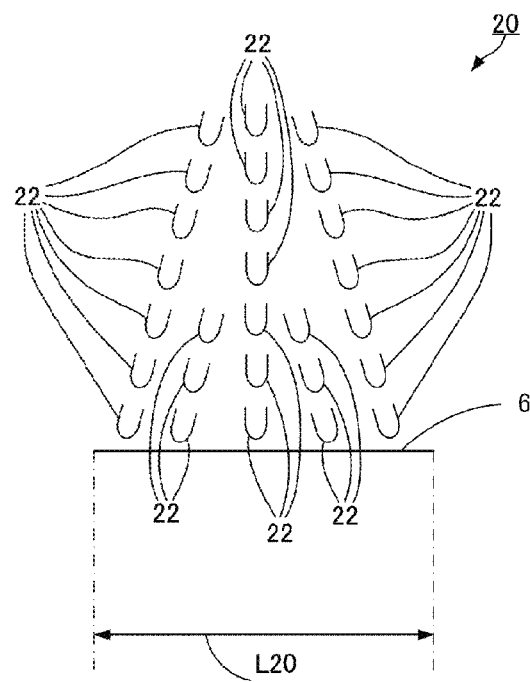

[Figure 7]
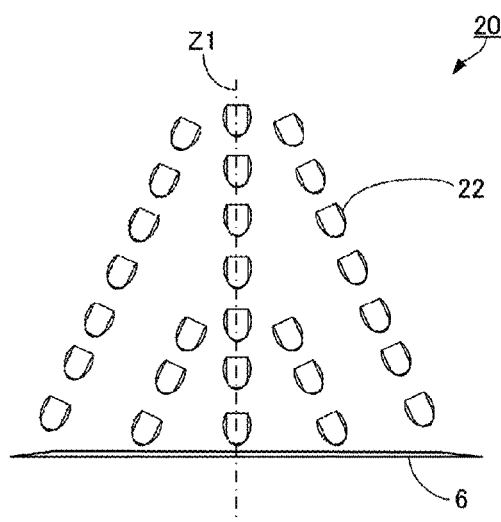
[Figure 8]
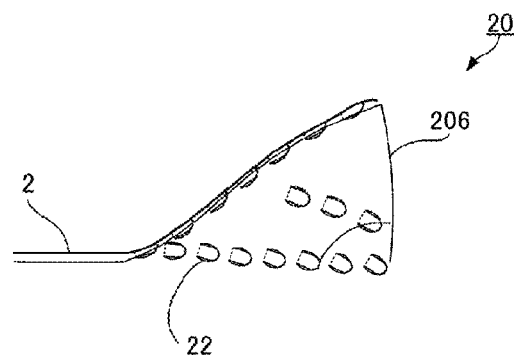
[Figure 9]
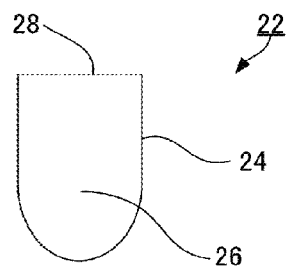

[Figure 10]
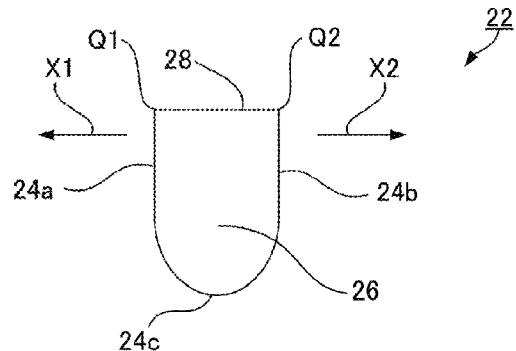
[Figure 11]
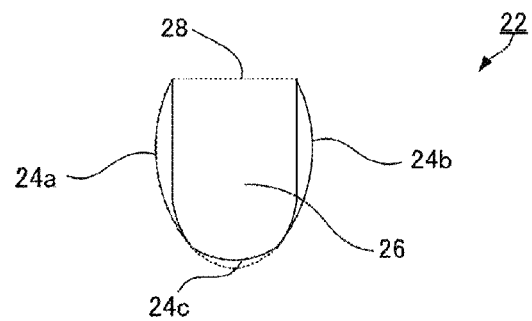
[Figure 12]
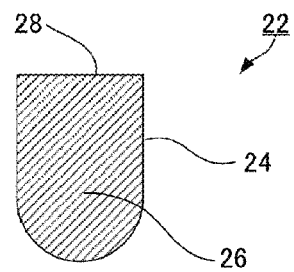
[Figure 13]
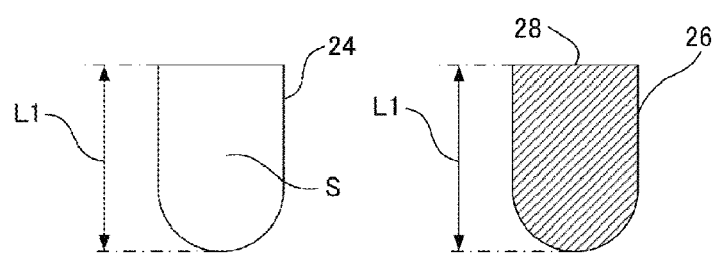

[Figure 14]
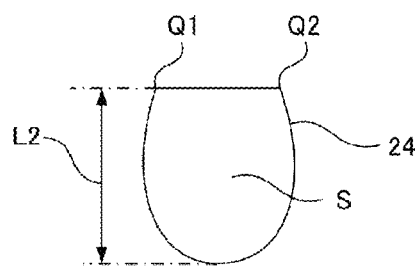
[Figure 15]
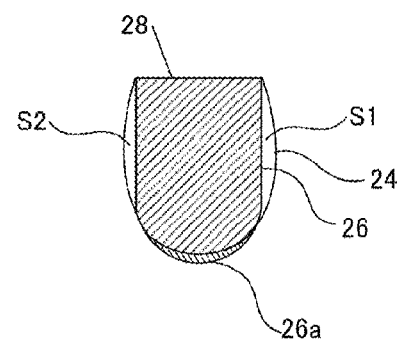
[Figure 16]
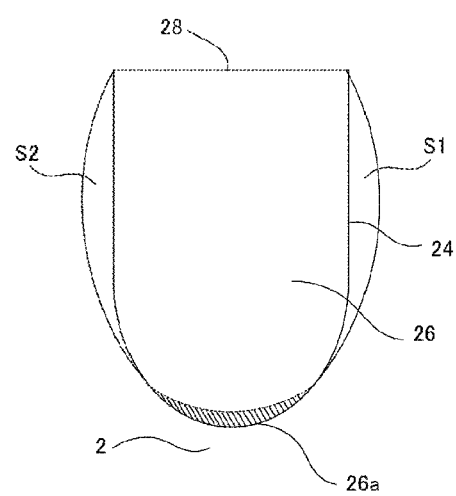

[Figure 17]
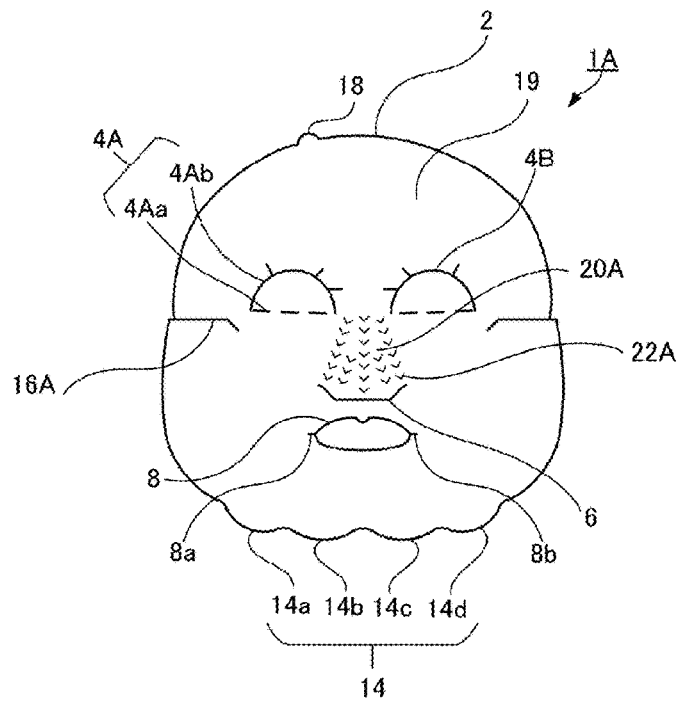
[Figure 18]
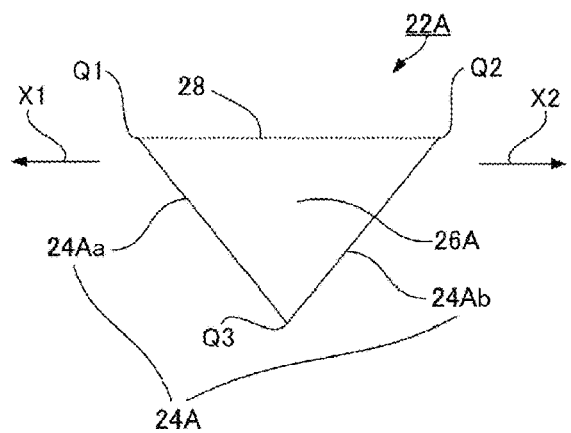
[Figure 19]
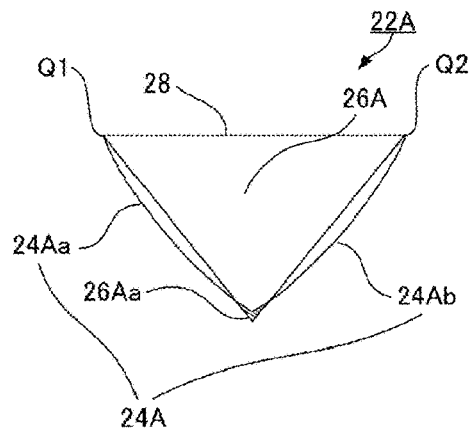

[Figure 20]
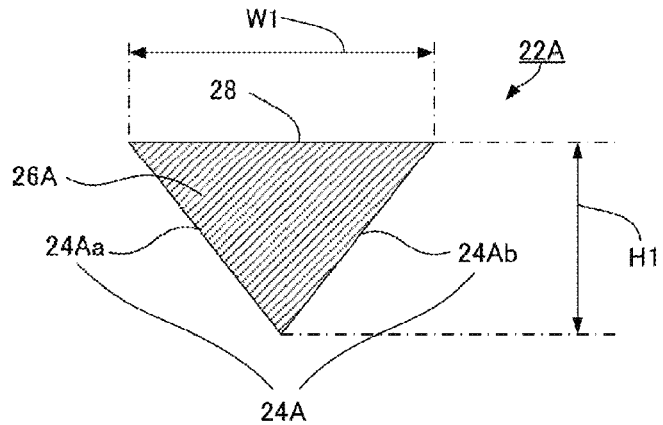
[Figure 21]
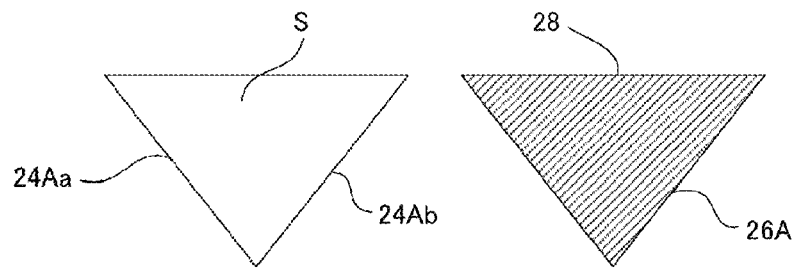
[Figure 22]
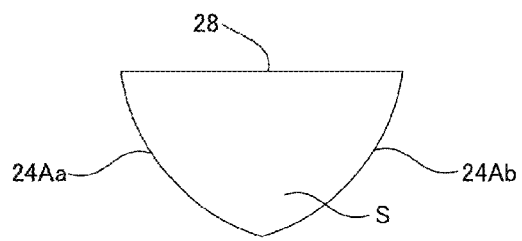
[Figure 23]
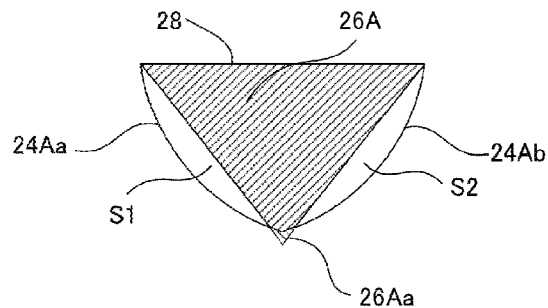

[Figure 24]
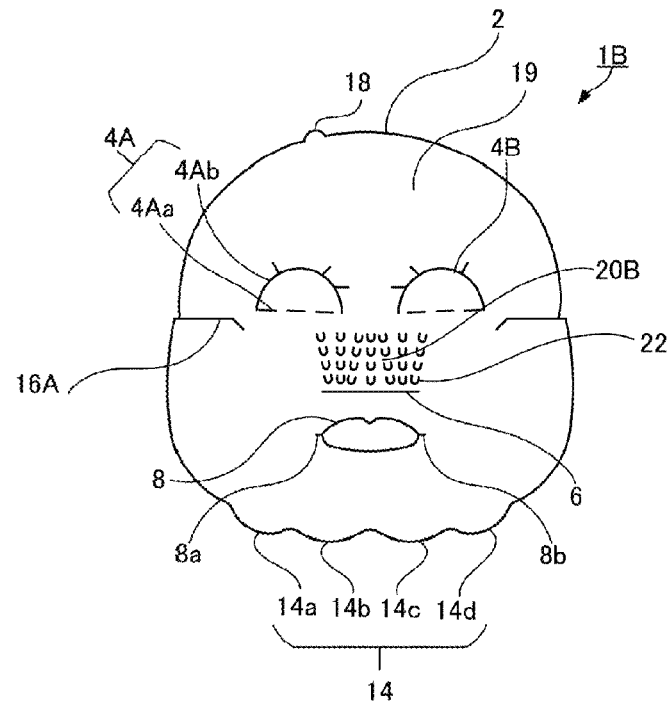
[Figure 25]
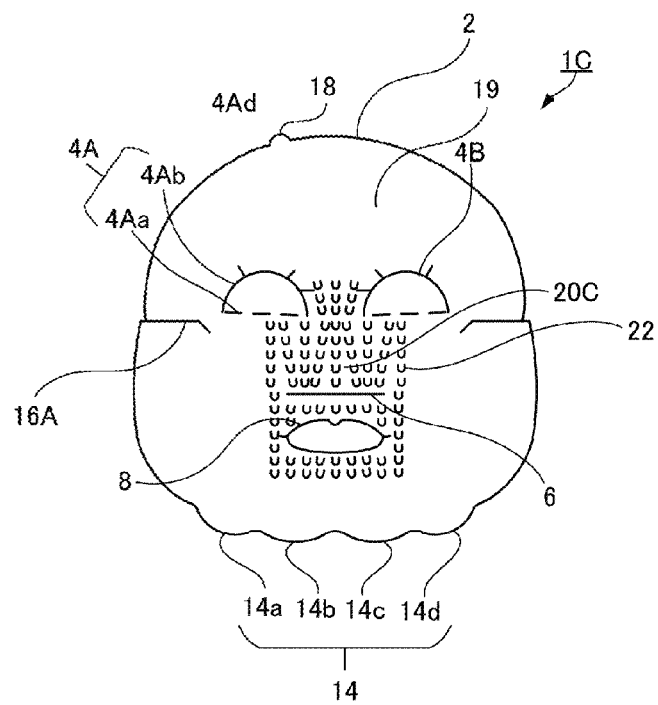

[Figure 26]
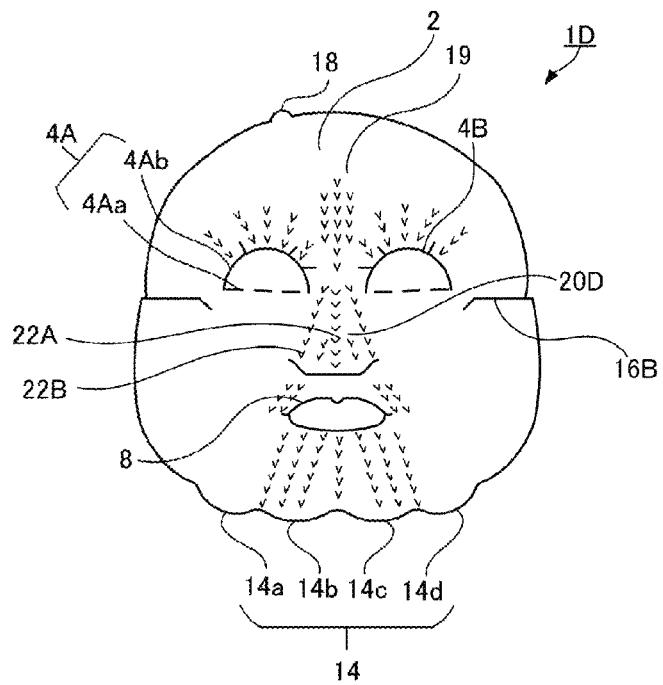
[Figure 27]
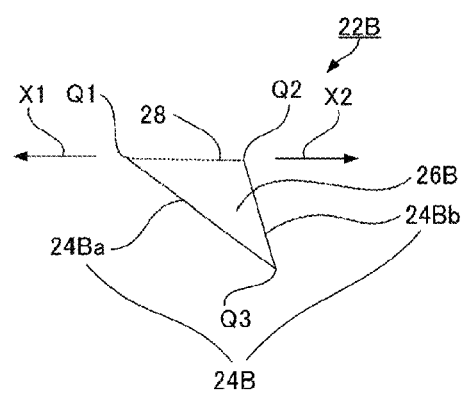
[Figure 28]
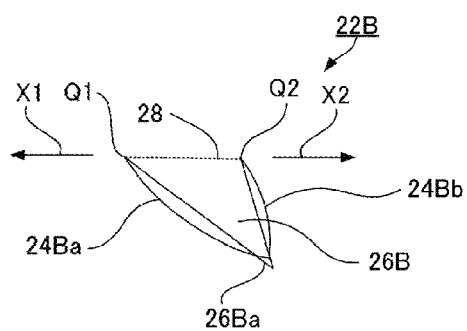

[Figure 29]
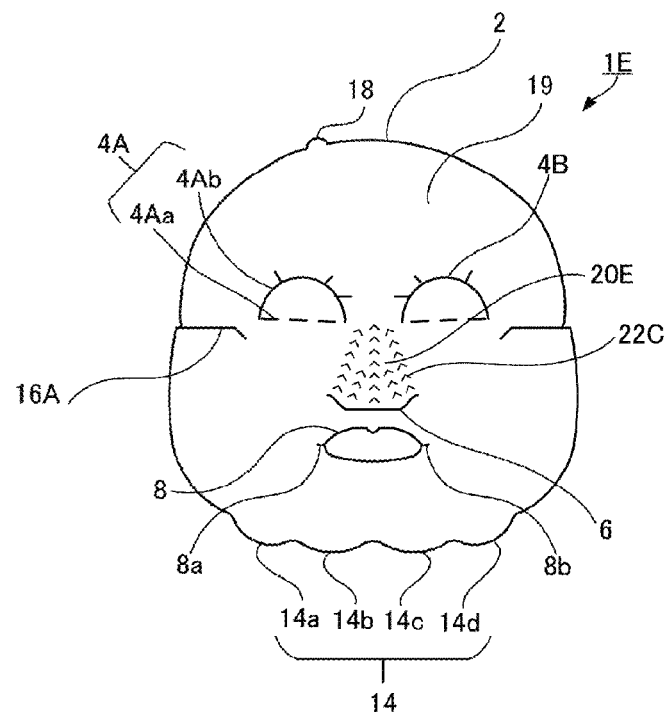
[Figure 30]
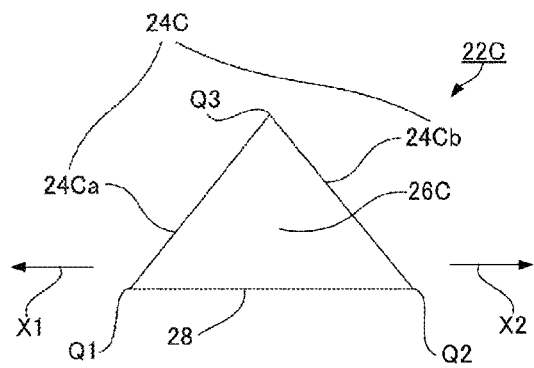
[Figure 31]
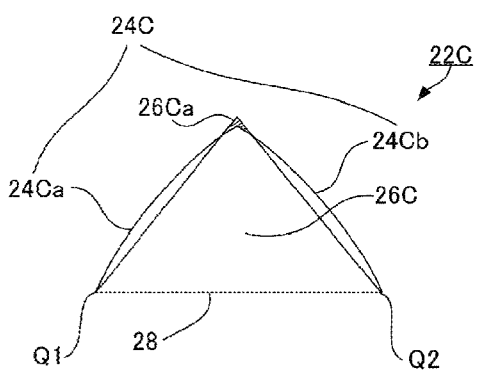

[Figure 32]
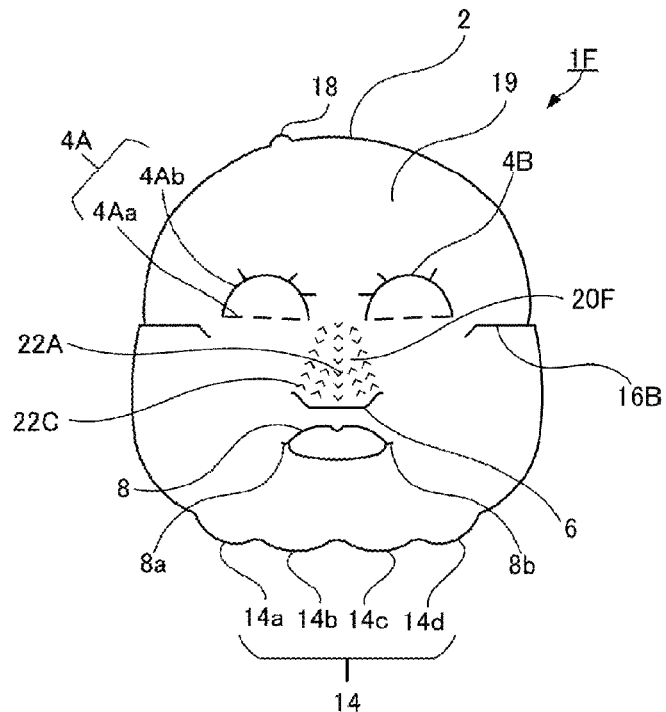
[Figure 33]
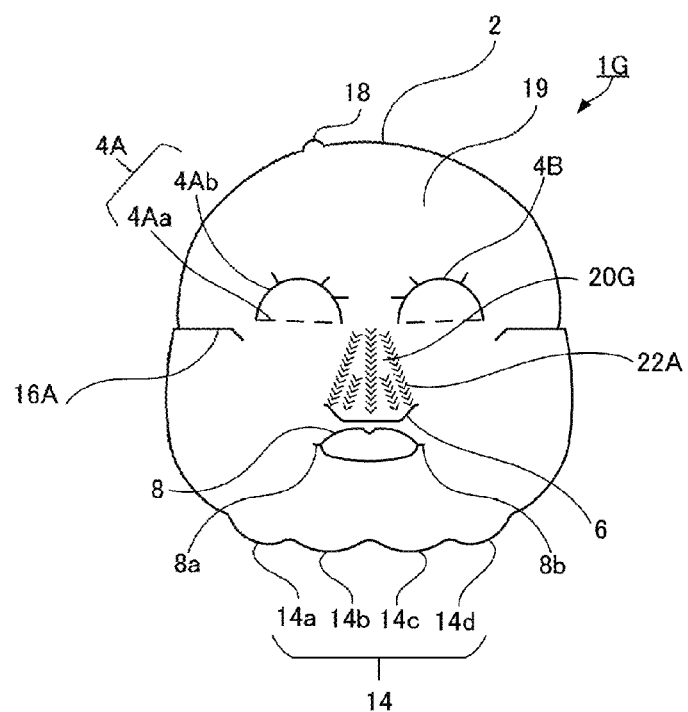

[Figure 34]
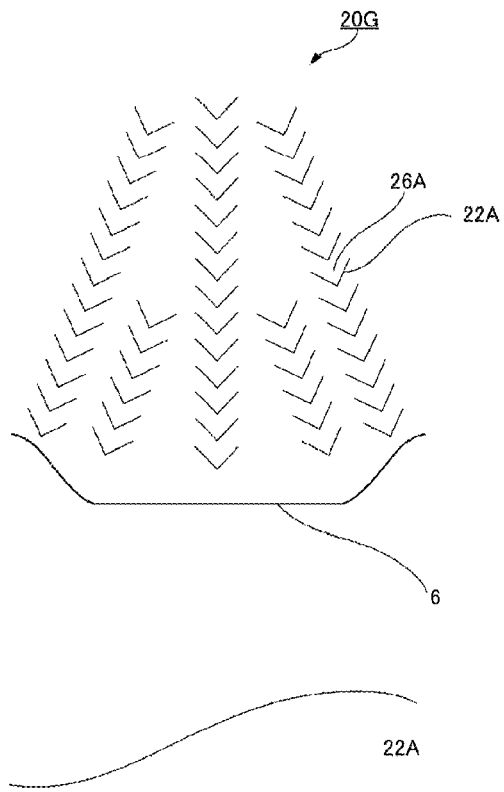
[Figure 35]
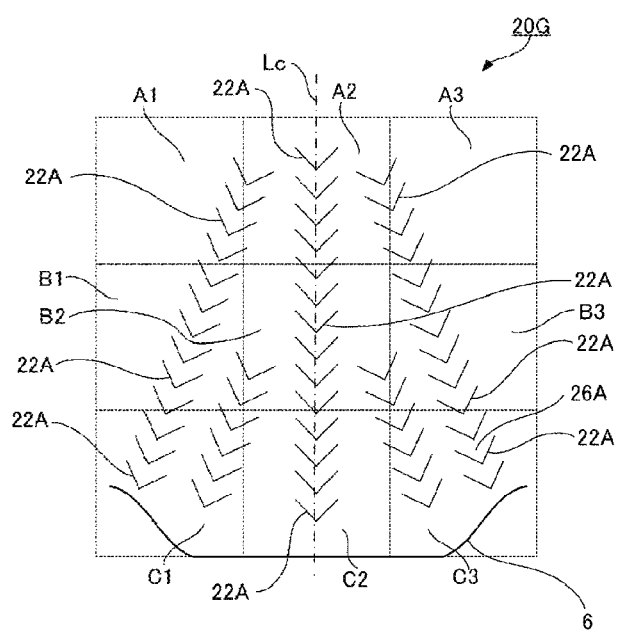

[Figure 36]
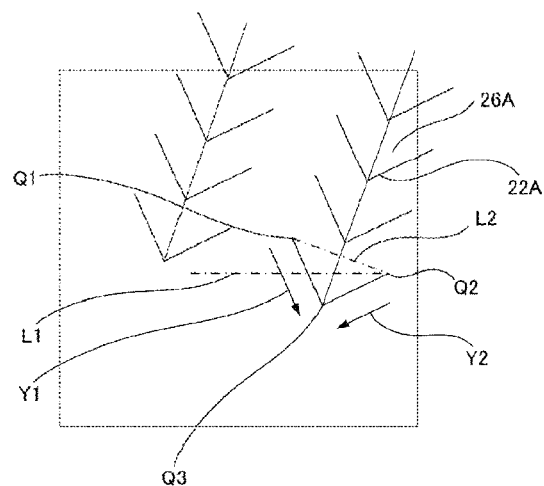
[Figure 37]
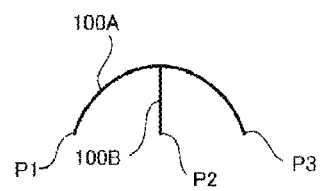
[Figure 38]
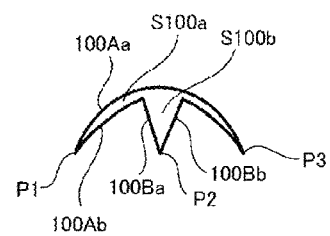
[Figure 39]
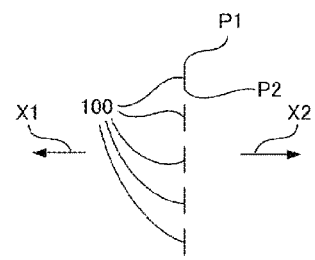

[Figure 40]
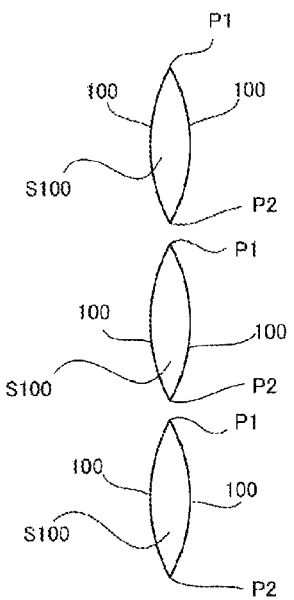

FACE MASK

TECHNICAL FIELD

The present invention is related to a face mask for beauty treatment purposes.

BACKGROUND ART

Conventionally, a face mask for facial use formed with a base material sheet impregnated with a cosmetic composition such as a cosmetic lotion have been used for beauty treatments (for example, Patent Documents 1 and 2). In addition, a nasal pack having improved adhesion to the nasal alae has been proposed (for example, Patent Document 3). Furthermore, in order to cover the user's nose with the face mask, a technique has been proposed in which a perforated cut line is formed in the nose of the face mask without forming a cut in the nasal contour of the face mask (for example, Patent Document 4).

CITATION LIST

Patent Literature

Patent Document 1 JP 2012-40250 A
Patent Document 2 JP 2009-240788 A
Patent Document 3 Utility Model Registration No. 3128445
Patent Document 4 JP 4352416 B

SUMMARY OF INVENTION

Technical Problem

None of the above-mentioned techniques can sufficiently cover at a relatively high conspicuous position a user's nose portion which has a convex and concave shape with a mask or pack to provide care with a cosmetic composition. Some of the above-described techniques only allow the mask or pack to follow the shape of the face and cannot provide sufficient care with the cosmetic composition. That is, when the mask or pack is made to follow the shape of the face, a space is generated in the mask or pack, and the user's face corresponding to the portion of the space cannot be cared for with the cosmetic composition. For example, in the techniques of Patent Documents 1 and 2, to accommodate the difference in height between the nose and the surrounding portion (hereinafter referred to as "height difference"), cuts are formed in the face mask to define the external shape of the nose corresponding to the contour of the user's nose, and when the face mask is applied, depending on the height difference, the cuts expand to create a space and in that space develops a state where the face mask is not covering the face. Since the cuts formed to define the external shape of the nose portion change shape in accordance with the height difference, there is no overlapping of the fabric of the face mask on both sides of the cuts. Further, with technology described in Patent Document 3, a cut illustrated in FIG. 37 is formed at the position of the pack corresponding to the nasal alae of the user. As illustrated in FIG. 37, the cut is formed by connecting a straight line cut 100B having an origin point P2 to an intermediate portion of the cut 100A connecting the points P1 and P3. When the portions of cuts 100A and 100B in FIG. 37 come into contact with the user's nose, due to the difference in height between the nasal alae and the surrounding portion (hereinafter referred to as "nasal alar height difference"), as illustrated in FIG. 38, cut 100A separates into cuts 100Aa and 100Ab creating a space S100*a*, and cut 100B separates into cuts 100Ba and 100Bb, creating a space S100*b*. In the space S100*a* and the space S100*b*, the nasal pack does not cover the nasal alae. The space S100*b* is likely to be the relatively highest position of the nasal alae and corresponds to a conspicuous portion. At this time, the cuts 100A and 100B do not change shape due to the nasal alar height difference, and there is no overlapping of the pack fabric on both sides of the cuts 100A and 100B. That is, with the technology of Patent Document 3, the nasal alar portion cannot be sufficiently covered by the nose pack, and moreover the most conspicuous portion cannot be covered. Furthermore, with the face mask of Patent Document 4, for example, as shown in FIG. 39, a plurality of line segment-shaped cuts (slits) 100 are arranged in a row. When the lateral force indicated by the arrows X1 and X2 acts on the slit 100 shown in FIG. 39, the slit 100 spreads left and right starting from the origin point P1 and the end point P2 of the slit 100 as illustrated in FIG. 40 and develops a gap S100. The gap S100 is relatively high in the user's nose portion which has concave and convex portions and is likely to occur in a conspicuous location. That is, in any of the face masks or nasal packs described above, it is difficult to care for a conspicuous portion with the cosmetic composition.

Based on the above, the present invention provides a face mask that can care for a conspicuous portion with a cosmetic composition on the face of a user having concave and convex portions.

Solution to Problem

A first invention is a face mask for beauty treatment purposes impregnated with a cosmetic composition, wherein the face mask is configured to cover the entire face of a user, and when a line tangent to a line segment connecting from the center of a forehead of a user with the center of a jaw of a user is given as a center line, in a nose portion which comes into contact with a nose of the user, a plurality of adjustment structures which are formed independently of each other are arranged in a portion on the left side of the center line and in a portion on the right side thereof, respectively; wherein the adjustment structures, which are formed independently of a cut defining the external shape of the nose portion, have a space boundary portion, which has as origin points two points in a direction different from the direction of the center line, forming a space through a cut connecting either below or above the two points, and a non-moving portion, which is of a same shape as the space, connected with the face mask main body at a location connecting the two points and arranged in the space; and are configured so that when the manner in which the face mask is applied to the face of the user is adjusted, the space boundary portion changes shape and the space expands to allow the non-moving portion to cover a region including a central portion of the space.

According to the configuration of the first invention, adjustment structures are formed independent of a cut that defines the external shape of the nose portion. As a result, when the face mask is applied to the user, compared to the case where the adjustment structures are continuous with cuts defining the external shape of the nose portion, the effect of the change in shape due to the difference in height (height difference) between the user's nose and its surroundings is relatively small. In the nose portion, a plurality of adjustment structures are arranged in each of the portion on the left side of the center line and the portion on the right side thereof, respectively. As a result, the height difference is adjusted by a plurality of adjustment structures. Accordingly, while the space boundary portion changes shape and the space expands as the manner in which the face mask in applied is adjusted on the user's face, since the degree of expansion of the respective spaces is relatively small when compared to the case of a single adjustment structure in the portion on the left side or portion on the right side, it allows the user's face to be more effectively cared for with the cosmetic composition. Furthermore, since the non-moving portion covers the area including the center of the expanded space, the user's face can be more effectively cared for with the cosmetic composition. Here, the expanded space is relatively high in the concavity and convexity of the user's nose and is likely to occur in a conspicuous location. In addition, the non-moving portion covers the region including the central portion of the expanded space. Through this, according to the configuration of the present invention, it allows conspicuous locations in the user's face which have concave portions and convex portions to be cared for with the cosmetic composition.

A second invention is the face mask according to the configuration of the first invention, wherein the plurality of adjustment structures formed independently of each other are arranged in a portion on the left side and a portion on the right side, respectively, of the center line in the nasal alar portion coming into contact with nasal alae of the user.

According to the configuration of the second invention, in the nasal alar portion which comes into contact with the nasal alae, since a plurality of adjustment structures formed independently of each other are arranged on each of the left portion and the right portion of the center line, the difference between the height of the user's nasal alae and the surrounding portion (nasal alar height difference) is adjusted through the plurality of adjustment structures. As a result, when the manner in which the face mask is applied is adjusted on the user's face, while the space boundary portion changes shape and the space expands, in comparison with the case where a single adjustment structure is formed on the nasal alar portion, or the adjustment structures are continuous, each respective space is relatively small, and moreover, the non-moving portion covers a region including the central portion of the expanded space. The expanded space is relatively high in the concavity and convexity of the user's nose and is likely to occur in a conspicuous location. The non-moving part also covers the area including the central portion of the expanded space.

A third invention is the face mask according to the configuration of the second invention, wherein in the nasal alar portion, a plurality of the adjustment structures are arranged in the up-down direction and/or the left-right direction independently of each other.

According to the configuration of the third invention, in the nasal alar portion, since the plurality of adjustment structures are arranged in the up-down direction and/or the left-right direction independently of each other, the complicated shape of the nasal alae can be followed in fine detail and, moreover, the highest and most conspicuous position can be reliably covered with a non-moving portion to allow care with a cosmetic composition.

A fourth invention is the face mask according to any one of the configurations of the first through third inventions, wherein the non-moving portion is configured so as to form an overlapping region which overlaps a portion of the face mask below or above the space boundary portion when the space boundary portion changes shape and expands in accordance with the shape of the nose of the user and the non-moving portion covers a region including a central portion of the space boundary portion.

According to the configuration of the fourth invention, since the overlapping area is formed, the face of the user can be more effectively cared for with the cosmetic composition in the area of the face mask below or above the space boundary portion.

Effect of the Invention

According to the face mask of the present invention, a conspicuous portion can be cared for with a cosmetic composition on the face of a user having concavities and convexities.

BRIEF DESCRIPTION OF THE DRAWINGS

FIG. 1 is a schematic plan view of a face mask according to a first embodiment of the present invention.

FIG. 2 is a schematic side view of a face mask.

FIG. 3 is a schematic view illustrating a face mask user's face.

FIG. 4 is a schematic view illustrating a state in which a face mask is applied to a user's face.

FIG. 5 is a schematic view illustrating a state in which a face mask is applied to a user's face.

FIG. 6 is a schematic view illustrating a nose portion of a face mask.

FIG. 7 is a schematic view illustrating a nose portion in a state where a face mask is applied to a user's face.

FIG. 8 is a schematic view of the nose portion of the face mask applied to the user's face as seen from the side.

FIG. 9 is a schematic diagram illustrating an adjustment structure.

FIG. 10 is a schematic diagram illustrating an adjustment structure.

FIG. 11 is a schematic diagram illustrating an adjustment structure.

FIG. 12 is a schematic diagram illustrating an adjustment structure.

FIG. 13 is a schematic diagram illustrating an adjustment structure.

FIG. 14 is a schematic diagram illustrating an adjustment structure.

FIG. 15 is a schematic diagram illustrating an adjustment structure.

FIG. 16 is a schematic diagram illustrating an adjustment structure.

FIG. 17 is a schematic plan view of a face mask according to a second embodiment of the present invention.

FIG. 18 is a schematic diagram illustrating an adjustment structure.

FIG. 19 is a schematic diagram illustrating an adjustment structure.

FIG. 20 is a schematic diagram illustrating an adjustment structure.

FIG. 21 is a schematic diagram illustrating an adjustment structure.

FIG. 22 is a schematic diagram illustrating an adjustment structure.

FIG. 23 is a schematic diagram illustrating an adjustment structure.

FIG. 24 is a schematic plan view of a face mask according to a third embodiment of the present invention.

FIG. 25 is a schematic plan view of a face mask according to a fourth embodiment of the present invention.

FIG. 26 is a schematic plan view of a face mask according to a fifth embodiment of the present invention.

FIG. 27 is a schematic diagram illustrating an adjustment structure.

FIG. 28 is a schematic diagram illustrating an adjustment structure.

FIG. 29 is a schematic plan view of a face mask according to a sixth embodiment of the present invention.

FIG. 30 is a schematic diagram illustrating an adjustment structure.

FIG. 31 is a schematic diagram illustrating an adjustment structure.

FIG. 32 is a schematic plan view of a face mask according to a seventh embodiment of the present invention.

FIG. 33 is a schematic plan view of a face mask according to an eighth embodiment of the present invention.

FIG. 34 is a schematic view illustrating an expanded nose portion.

FIG. 35 is a schematic view illustrating a nose portion divided into a plurality of parts.

FIG. 36 is a schematic view illustrating an expanded nasal alar portion.

FIG. 37 is a schematic view illustrating a conventional example.

FIG. 38 is a schematic view illustrating a conventional example.

FIG. 39 is a schematic view illustrating a conventional example.

FIG. 40 is a schematic view illustrating a conventional example.

DESCRIPTION OF EMBODIMENTS

First Embodiment

Preferred embodiments of the present invention will be described below with reference to the drawings. Note that description of configurations that can be appropriately implemented by those skilled in the art will be omitted, and only the basic configuration of the present invention will be described.

As illustrated in FIG. 1, a face mask 1 is composed of a base material sheet 2. The base material sheet 2 is formed of, for example, a nonwoven fabric. Examples of the material for the nonwoven fabric include polyester, nylon, polyethylene, polypropylene, polyvinyl alcohol, cotton, Cupra, rayon, and pulp. The base material sheet 2 is impregnated with a cosmetic composition. The main component of the cosmetic composition is moisture, and further contains at least one of the following beauty treatment components: human oligopeptide-1, human oligopeptide-13, acetylhexapeptide-8, palmitoylpentapeptide-4, water-soluble collagen, hydrolyzed collagen, succinoyl atelocollagen, magnesium ascorbyl phosphate, saccharomyces (black sugar, placenta extract) ferment solution, sodium hyaluronate, sodium acetylated hyaluronate, sodium hyaluronate crosspolymer, cerebroside, arbutin, magnesium aspartate, dipotassium glycyrrhizate, copper gluconate, zinc gluconate, placenta extract, saitai extract, water-soluble proteoglycan, platinum, sake cake extract, Iwabenkei root extract, apple fruit cultured cell extract, vitamin A oil, tocopherol, *Saccharomyces cerevisiae* extract, cerebroside, PCA-Na, natto gum, avocado oil, kaninabara fruit oil, apricot kernel oil, sunflower seed oil, sodium lysine dilauroyl glutamate, aminocaproic acid, or betaine.

In FIG. 1, the surface of the page facing toward the reader is the front surface 1Aa of FIG. 2; the reverse side of the page is the back surface 1Ab of FIG. 2. When the face mask 1 is used, the back surface 1Ab comes into contact with the face of a user. The face mask 1 is configured (see FIGS. 4 and 5) to cover the entire face of a user 200 (see FIG. 3).

On the base material sheet 2, there are formed eyelid portions 4A and 4B, a nose portion 20, a mouth portion opening 8, a jaw portion 14, side portion cuts 16A and 16B, and a protruding portion 18 for denoting upper/lower, left/right, and front/back directionality of the face mask 1. A linear horizontal cut (slit) 6 is formed below the nose portion 20. On the base material sheet 2, the portion that comes into contact with the forehead of the user 200 is a forehead portion 19.

In the present specification, the direction of the face mask 1 in which the forehead portion 19 is formed is referred to as upper (upward); the direction in which the jaw portion 14 is formed is referred to as lower (downward); the direction in which the side portion cuts 16A and 16B are cut as viewed from the nose portion 20 is referred to as outside (sideward); and the direction from the outside toward the nose portion 20 is referred to as the center direction. In the face mask 1, a virtual line that is in contact with a line segment that connects the center of the user's forehead to the center of the user's mouth is referred to as a "center line". The direction from the upper side to the lower side is referred to as vertical direction. The vertical direction includes the direction of the nasal muscles but does not exactly coincide with the center line. On the surface of the face mask 1, a direction perpendicular to the vertical direction is referred to as horizontal direction. When referring to "upward" with respect to a certain configuration, the upper side is not limited to being located on the upper side along a line parallel to the center line and may be on an upper side shifted to the left and/or right. Similarly, when referring to "downward" with respect to a certain configuration, it is not limited to being positioned on the lower side along a line parallel to the center line but may be on a lower side shifted to the left and/or right. In addition, when referring to "left" or "right" for a certain configuration, it is not limited to being positioned on the left or right side along a line perpendicular to the center line but may be on the left or right side shifted up and/or down. Further, a portion where no cut or opening is formed is referred to as a "main body portion" of the base material sheet 2.

The surface of the human face is three-dimensionally shaped with convex and concave portions. The shapes of the convex and concave portions are different depending on the facial part, and in each part, a relatively high portion becomes a convex portion and a relatively low portion becomes a concave portion. In the region near the nose and including the nose itself, the degree of convexity/concavity is remarkable.

The nose portion 20 of the face mask 1 is the portion that comes into contact with the user's nose. In the nose portion 20A, a plurality of adjustment structures 22 for adjusting the convexity/concavity of the user's nose are formed independently of each other. Further, the adjustment structures 22 are not continuous with the lower cut 6 that defines the outline of the nose portion 20 and are formed independently.

Since the cosmetic composition is impregnated into the face mask 1, it sticks to the user's face. When the face mask 1 is applied, the face mask 1 is first placed in contact with the forehead, eyes, nose, and the like, and then applied in accordance with the shape of the face such as the cheek, mouth, and jaw. The face mask 1 is made larger than the average human face.

In general, when a planar face mask is matched to a three-dimensional facial shape, wrinkling and sagging portions develop on the face mask, and the face mask may peel off from the face or lift from the face. In order to cope with the problem of peeling and lifting, it is necessary to finely adjust application of the face mask. In order to finely adjust the face mask, it is necessary to shift the already sticking face mask and make it slide upon the face, or alternately, to shift the face mask by gripping and removing a portion of the face mask. In this respect, according to the face mask 1, through the above-described adjustment structures 22 and the side portion cuts 16A etc., it is possible to easily adjust after initial placement and effectively apply to the face while preventing wrinkling and sagging of the face mask 1.

Each configuration of the face mask 1 will be described in detail below.

<Configuration Near the Eyelids>

The base material sheet 2 is formed with eyelid portions 4A and 4B which cover the user's eyelids (see FIG. 1). The eyelid portion 4A is continuous with the base material sheet 2 at the linear line segment portion 4Aa. In addition, the eyelid portion 4A is separated from the main body portion of the base material sheet 2 at the time of use by a substantially arc-shaped eyelid portion cut 4Ab. The eyelid portion 4A can cover the entire eyelid of the user as a shuttered portion (see FIG. 4), or it can be folded near the line segment portion 4Aa and used as a folded portion (see FIG. 5). It is configured so as to be folded at the edge of the eye in accordance with the size of the user's eye to provide intensive care in the portion below the user's lower eyelid. The configuration of the eyelid portion 4B is the same as that of the eyelid portion 4A.

<Configuration Near the Nose>

In the base material sheet 2, a plurality of adjustment structures 22 (see FIG. 6 and the like) are formed independently of each other on a nose portion 20 which comes into contact with the user's nose. Further, the adjustment structures 22 are not continuous with the lower cut 6 which defines the outline of the nose portion 20 and are formed independently. The adjustment structures 22 are in the state illustrated in FIGS. 1 and 6 before being applied to the face. The adjustment structures 22 are configured to change shape as illustrated in FIGS. 4, 5, 7, and 8 and conform to the nose 206 of the user 200 as the face mask 1 is applied to the face of the user 200 and the manner in which it is applied is adjusted. Hereinafter, the configuration of the adjustment structures 22 will be described in detail.

As described above, the adjustment structures 22 are configured to change shape as illustrated in FIGS. 7 and 8 and conform to the nose 206 of the user 200 as the face mask 1 is applied to the face of the user 200 and the manner in which it is applied is adjusted. Hereinafter, the configuration of the adjustment structures 22 will be described in detail.

As illustrated in FIG. 9, the adjustment structure 22 includes a space boundary portion 24, a non-moving portion 26, and a connecting portion 28. The space boundary portion 24 is a slit formed by cutting the base material sheet 2. The non-moving portion 26 is a portion that is generated as a result of the formation of the space boundary portion 24 and is connected to the main body portion of the base material sheet 2 by the connecting portion 28.

As illustrated in FIG. 10, the space boundary portion 24 has as its origin points two points Q1 and Q2 which separate from each other in a direction other than the direction of the nasal muscle, and is formed by the cuts 24a and 24b which are connected with the lower portion 24c downward of those two points. The space boundary portion 24 is formed in a U shape.

The non-moving portion 26 has the same shape as the space defined by the space boundary portion 24 in the state before being applied to the user 200. As described above, the non-moving portion 26 is connected to the main body portion of the base material sheet 2 by the connecting portion 28. The connecting portion 28 is a line segment connecting the two points Q1 and Q2.

The non-moving portion 26 is an area having the space boundary portion 24 and the connecting portion 28 as its outer perimeter. The non-moving portion 26 is configured to cover an area including the center of the space defined by the space boundary portion 24 when the space boundary portion 24 changes shape in accordance with the shape of the nose 206 of the user 200.

In each adjustment structure 22, the direction towards each end from the center of the line segment connecting the two points Q1 and Q2 of the space boundary portion 24 (hereinafter referred to as "line segment direction") is formed to match the direction of force acting on the space boundary portion 24 when the face of the user 200 is covered with the face mask 1 and the space boundary portion 24 changes shape in accordance with the shape of the nose 206 of the user 200.

The direction of the force acting on the space boundary portion 24 is analyzed for each part of the nose portion 20 that is in contact with each part of the nose 206 of the user 200, and the line segment direction is formed to match the direction of the force. For this reason, the line segment direction is not necessarily uniform among the plurality of adjustment structures 22. Depending on the position and shape of each part of the nose 206 of the user 200, the line segment direction of the two points Q1 and Q2 is configured to match the direction of the force acting on the adjustment structure 22, that is, the arrow X1 direction and the direction indicated by the arrow X2.

The length of the line segment connecting the two points Q1 and Q2 of the face mask 1 is defined as a length less than one third of the length L20 (see FIG. 6) of the longest portion of the nose portion 20 in the left-right direction. Therefore, at least three adjustment structures 22 can be arranged in parallel in the longest portion. In the example of FIG. 1, five adjustment structures 22 are arranged in parallel at the longest portion.

As described above, since it is configured so that the line segment direction of the line segment connecting the points Q1 and Q2, which are the origin points of the space boundary portion 24, matches the direction of the force acting on the space boundary portion 24 when the face mask 1 covers the face of the user 200 and the space boundary portion changes shape in accordance with the shape of the nose 206 of the user 200, the left-right force acting on the non-moving portion 26 is cancelled out without the non-moving portion 26 traveling significantly and without significantly changing shape. For this reason, as illustrated in FIG. 11, the non-moving portion 26 covers a region including the central portion of the space defined by the space boundary portion 24 when the space boundary portion 24 changes shape and the space expands. In addition, since a plurality of adjustment structures 22 are formed, each adjustment structure 22 only changes shape a relatively small amount compared to the case of only a single adjustment structure 22.

In the adjustment structures 22 illustrated in FIGS. 12 to 15, the non-moving portion 26 is indicated by hatching (a plurality of parallel oblique lines). When the adjustment structure 22 of FIG. 12 is analyzed, as illustrated in FIG. 13, a space S defined by the space boundary portion 24 and the non-moving portion 26 having the same shape as the space S are obtained. The non-moving portion 26 is connected to the main body portion of the base material sheet 2 by a connecting portion 28. The length in the vertical direction of the space S and the non-moving portion 26 is defined as a length L1.

When the face mask 1 is applied to the face of the user 200, a force in the line segment direction of the points Q1 and Q2 which are the origin points of the space boundary portion 24 acts, and as illustrated in FIG. 14, the space boundary portion 24 changes shape in the line segment direction of origin points which are the points Q1 and Q2 and the space S expands. As a result, the length of the space S becomes shorter than the initial length L1 and becomes the length L2.

Meanwhile, the non-moving portion 26 is independent from the main body portion of the face mask 1 except for the connecting portion 28. For this reason, the force acting on the space boundary portion 24 does not directly act on the non-moving portion 26 except for the connecting portion 28. In addition, since both ends of the connecting portion 28 have substantially the same size and a force in the opposite direction acts, the non-moving portion 26 does not move significantly, there is no significant change in shape, and the length of the non-moving portion 26 substantially maintains the initial length L1. As a result, as illustrated in FIG. 15, the non-moving portion 26 covers a region including the center of the expanded space S. As a result, most of the space S is covered with the non-moving portion 26, and only small spaces S1 and S2 which are portions of the space S are not covered with the base material sheet 2.

As described above, since the length of the space S is shorter than the initial length L1, while the non-moving portion 26 substantially maintains the initial length L1 and maintains a position that sticks to the face of the user 200 and hardly moves, as illustrated in FIGS. 15 and 16, when the non-moving portion 26 covers the expanded space S, the non-moving portion 26 overlaps with the main body portion of the base material sheet 2 below the space boundary portion 24 which has changed shape to form an overlapping region 26a. Since the base material sheet 2 is doubled in the overlapping region 26a, the portion of the face of the user 200 coming into contact with the overlapping region 26a can be cared for with more of the cosmetic composition.

As described above, the non-moving portion 26, by covering the expanded space S, not only reduces the area where the base material sheet 2 does not come into contact with the face of the user 200, but also by forming the overlapping region 26a makes it possible to care for portions of the face of the user 200 which come into contact with the overlapping region 26a with more of the cosmetic composition. When the center line is a line that touches a line segment that connects the center of the forehead of the user 200 to the center of the mouth of the user 200, in the nose portion 20 which comes into contact with the nose 206 of the user 200, the plurality of adjustment structures 22 are formed independently of each other on left side of the center line and the right side of the center line, respectively. Each adjustment structure 22 is formed independently of a cut that defines the external shape of the nose portion 20. In the present embodiment, the cut defining the external shape of the nose portion 20 is a line segment shaped cut 6 of the lower part of the nose portion 20. Since the influence of the height difference on the adjustment structure 22 is relatively small, and a plurality of adjustment structures 22 are formed, the influence of the height difference and the nose height difference on each adjustment structure 22 is further relatively small. As a result, the degree of change of shape of each of the adjustment structures 22 is relatively small. For example, when the area of one large space and the total area of a plurality of small spaces are the same, while the cosmetic composition can exude from the base material sheet 2 and cover it if it is a small space, in the case of a single large space, it is difficult. A configuration in which a plurality of small spaces are formed, in addition to being effective in following the shape of the face, is also effective in covering the face with the cosmetic composition. Furthermore, as described above, each adjustment structure 22 has a space boundary portion 24 having as its origin points two points separated from each other in a direction other than the direction of the center line and forming the space S by the cut coming into contact above or below those two points and a non-moving portion 26 which has the same shape as the space S and is connected with the main body portion of the face mask 1 at the location where the two points are connected, and arranged on space S, and is configured so that the space boundary portion 24 can change shape, the space S can expand and the non-moving portion 26 can cover the region which includes the central portion of space S when the manner with which the face mask 1 is applied to the face of the user 200 is adjusted. As a result, a user's face can be more effectively cared for with the cosmetic composition.

<Configuration of the Mouth>

A mouth portion opening 8 corresponding to the user's mouth portion is formed in the base material sheet 2 (see FIG. 1). At both ends of the mouth portion opening 8, end portion cuts 8a and 8b directed to the side are formed. Due to the end portion cuts 8a and 8b, it is easy to follow the shape of the mouth which varies from person to person.

<Configuration of the Jaw Portion>

The base material sheet 2 is formed with a convex shaped jaw portion 14 which comes into contact with a user's jaw portion (see FIG. 1). The jaw portion 14 is comprised of continuous convex portions 14a, 14b, 14c and 14d. As illustrated in FIGS. 4 and 5, when the face mask 1 is applied to the user 200, the jaw portion 14 is attached so as to be bent along the jaw of the user 200. At that time, the convex portions 14a and the like are brought near to the lower jaw and come into close contact with the jaw of the user 200 so as to be integrated.

<Configuration of the Sides>

Side portion cuts 16A and 16B are formed in the base material sheet 2 (see FIG. 1). The side portion cuts 16A and 16B are formed in a non-linear manner, which allows the face mask 1 to form into a curved portion to conform with the shape of the swell in the peripheral region having the cheek bone as its apex and the shape of the subsequent portion as the face mask 1 is applied to the face of the user 200.

Second Embodiment

A second embodiment will be described with reference to FIGS. 17 through 23, with a focus on differences from the first embodiment. Descriptions of items in common with the first embodiment will be omitted as appropriate.

As illustrated in FIG. 17, a nose portion 20A is formed in a face mask 1A. The nose portion 20A is formed of a plurality of adjustment structures 22A. As illustrated in FIGS. 18 to 23, with the adjustment structure 22A, a space boundary portion 24A is formed of straight line shaped cuts 24Aa and 24Ab. The space boundary portion 24A is formed in a V shape. The straight line shaped cuts 24Aa and 24Ab are connected at a point Q3 below the two points Q1 and Q2, starting from the two points Q1 and Q2 that are separated in a direction other than the direction of the nose muscle. The straight line shaped cuts 24Aa and 24Ab form an isosceles triangular shaped space S (see FIG. 21), and a non-moving portion 26A having the same shape as the space S is formed. In addition, the lower cut 6 below the nose portion 20A is formed in a shape in which the portions near both ends of the straight line segments are directed obliquely upward. The same applies to the cut 6 below a nose portion 20D, a nose portion 20E, and a nose portion 20F, which will be described later.

As illustrated in FIG. 18, the adjustment structure 22A includes a space boundary portion 24A, a non-moving portion 26A, and a connecting portion 28. The space boundary portion 24A is a slit formed by cutting the main body portion of the base material sheet 2. The non-moving portion 26A is a portion of the base material sheet 2 that is generated as a result of the formation of the space boundary portion 24A and is connected to the main body portion of the base material sheet 2 by the connecting portion 28.

The non-moving portion 26A has the same shape as the space defined by the space boundary portion 24A before being applied to the user 200. That is, the non-moving portion 26A is a region having the space boundary portion 24A and the connecting portion 28 as its outer perimeter. The non-moving portion 26A is configured to cover an area including the central portion of the space S when the space boundary portion 24A changes shape and the space S expands in accordance with the shape of the nose 206 of the user 200.

The line segment direction of the points Q1 and Q2 that are the origin points of the space boundary portion 24A is formed so as to coincide with the direction of the force acting on the space boundary portion 24A as the face mask 1A covers the face of the user 200 and the space boundary portion 24A changes shape in accordance with the shape of the nose of the user 200. As the face mask 1A changes shape in accordance with the shape of the nose of the user 200, forces act in the directions of arrows X1 and X2. The line segment directions of the points Q1 and Q2 coincide with the arrow X1 direction and the arrow X2 direction.

The length of the line segment connecting the points Q1 and Q2 which are the origin points of the face mask 1A is defined as one third or less the length of the longest portion of the nose portion 20A in the left-right direction.

As described above, since the line segment direction of the points Q1 and Q2, which are the origin points of the space boundary portion 24A, is formed so as to coincide with the direction of the force which acts upon the face mask 1A as the face mask 1A covers the face of the user 200 and the space boundary portions 24A change shape in accordance with the shape of the nose of the user 200, the non-moving portion 26A does not significantly shift or change shape. For this reason, as illustrated in FIG. 19, the non-moving portion 26A covers a region including the central portion of the space S defined by the space boundary portion 24A as the space boundary portion 24A changes shape and the space S expands.

In FIGS. 20, 21 and 23, the non-moving portion 26A is indicated by hatching (a plurality of parallel oblique lines). As illustrated in FIG. 20, the non-moving portion 26A is formed so that a width W1 is longer than a height H1. When the adjustment structure 22A of FIG. 20 is analyzed, as illustrated in FIG. 21, a space S defined by the space boundary portion 24A and the non-moving portion 26A having the same shape as the space S are obtained. The non-moving portion 26A is connected to the main body portion of the base material sheet 2 by the connecting portion 28.

As the face mask 1A is applied to the face of the user 200, as illustrated in FIG. 22, the space S changes shape and expands in the line segment direction of the origin points Q1 and Q2, and the length in the vertical direction is also shortened. In this case, since with the adjustment structure 22A, the non-moving portion 26A is configured so as not to significantly change shape or move, as illustrated in FIG. 23, the non-moving portion 26A covers the region including the center of the expanded space S. As a result, most of the space S is covered by the non-moving portion 26A, and only the small spaces S1 and S2 that are part of the space S are not covered by the base material sheet 2.

As illustrated in FIG. 23, when the non-moving portion 26A covers the expanded space S, the non-moving portion 26 A overlaps with the main body portion of the base material sheet 2 to form an overlapping region 26Aa. Since the base material sheet 2 is doubled in the overlapping region 26Aa, the part of the face of the user 200 in contact with the overlapping region 26Aa can be cared for with more of the cosmetic composition.

As described above, the non-moving portion 26A not only reduces the area where the base material sheet 2 does not come into contact with the face of the user 200 by covering the expanded space S, but also by forming the overlapping region 26Aa, more of the cosmetic composition can care for the portion of the face of the user 200 which is in contact with the overlapping region 26Aa.

Third Embodiment

A third embodiment will be described with reference to FIG. 24, with a focus on differences from the first embodiment. Descriptions of items in common with the first embodiment will be omitted as appropriate.

In a face mask 1B of the third embodiment, adjustment structures 22 (see FIGS. 9 to 11) are also formed outside a nose portion 20B. Through this, the base material sheet 2 can be brought into contact with the face via the adjustment structure 22s in regions other than the nose 206 of the user 200, for example, in the region between the nose and the cheekbone to allow care with the cosmetic composition.

Fourth Embodiment

A fourth embodiment will be described with reference to FIG. 25, with a focus on differences from the first embodiment. Descriptions of items in common with the first embodiment will be omitted as appropriate.

In a face mask 1C of the fourth embodiment, the adjustment structures 22 (see FIGS. 9 to 11) are disposed not only in the nose portion 20C but also around the eyes and mouth. Through this, the base material sheet 2 can be brought into contact with the face throughout the entire center region of the face of the user 200 via the adjustment structures 22 to allow care with the cosmetic composition.

Fifth Embodiment

A fifth embodiment will be described with reference to FIGS. 26 to 28, with a focus on differences from the first embodiment. Descriptions of items in common with the first embodiment will be omitted as appropriate.

In a face mask 1D, adjustment structures 22A (see FIG. 18 and the like) and adjustment structures 22B (see FIGS. 27 and 28) are formed. The adjustment structures 22A and the like are also formed in portions which come into contact with the forehead, the eye, and the jaw in addition to the nose portion 20D.

As illustrated in FIG. 27, an adjustment structure 22B includes a space boundary portion 24B, a non-moving portion 26B, and a connecting portion 28. The space boundary portion 24B is a slit formed by cutting the main body portion of the base material sheet 2. The space boundary portion 24B is formed in a deformed V shape. The non-moving portion 26B is a portion of the base material sheet 2 that develops as a result of the formation of the space boundary portion 24B and is connected to the main body portion of the base material sheet 2 by the connecting portion 28.

As illustrated in FIG. 27, the space boundary portion 24B is formed by cuts 24Ba and 24Bb that are connected at a point Q3 below two points Q1 and Q2, starting from the two points Q1 and Q2 that are separated in a direction different from the direction of the nose muscle.

The non-moving portion 26B has the same shape as the space defined by the space boundary portion 24B before being applied to the user 200. That is, the non-moving portion 26B is an area having the space boundary portion 24B and the connecting portion 28 as the outer perimeter. When the space boundary portion 24B changes shape and the space S expands in accordance with the shape of the nose 206 of the user 200, the non-moving portion 26B is configured to cover an area including the center of the space S defined by the space boundary portion 24B.

The line segment direction of the origin points Q1 and Q2 of the space boundary portion 24B is formed so as to coincide with the direction of the force acting on the space boundary portion 24B as the face mask 1D covers the face of the user 200 and changes shape in accordance with the shape of the nose of the user 200. When the space boundary portion 24B changes shape in accordance with the shape of the nose 206 of the user 200, forces in the directions of the arrows X1 and X2 are applied. The line segment directions of the origin points Q1 and Q2 are formed so as to coincide with the arrow X1 direction and the arrow X2 direction.

The length of the line segment connecting the origin points Q1 and Q2 is defined as one-third or less the length of the longest portion of the nose portion 20D in the left-right direction. Further, the length of the line segment connecting from the center of the line segment connecting the points Q1 and Q2 to the lowermost part Q3 is defined as a length longer than the length of the line segment connecting the points Q1 and Q2.

Sixth Embodiment

A sixth embodiment will be described with reference to FIGS. 29 through 31, with a focus on differences from the second embodiment. Descriptions of items in common with the second embodiment will be omitted as appropriate.

As illustrated in FIG. 29, a nose portion 20E is formed in a face mask 1E. The nose portion 20E is formed from a plurality of adjustment structures 22C (see FIGS. 30 and 31). As illustrated in FIGS. 30 and 31, in the adjustment structure 22C, the space boundary portion 24C is formed of straight line shape cuts 24Ca and 24Cb. The space boundary portion 24C is formed in an upside-down V-shape. The straight line shape cuts 24Ca and 24Cb have as their origin points the two points Q1 and Q2 which are separated in a direction other than the direction of the nose muscle, and are connected by a point Q3 above the two points Q1 and Q2. The straight line shape cuts 24Ca and 24Cb form an upright isosceles triangular space with apex upward, and a non-moving portion 26C having the same shape as the space is formed.

As illustrated in FIG. 30, an adjustment structure 22C includes a space boundary portion 24C, a non-moving portion 26C, and a connecting portion 28. The space boundary portion 24C is a slit formed by cutting the main body portion of the base material sheet 2. The non-moving portion 26C is a portion of the base material sheet 2 which develops as a result of the formation of the space boundary portion 24C and is connected to the main body portion of the base material sheet 2 by the connecting portion 28.

As illustrated in FIG. 31, when the non-moving portion 26C covers the expanded space, the non-moving portion 26C overlaps with the main body portion of the base material sheet 2 to form an overlapping region 26Ca. Since the base material sheet 2 is doubled in the overlapping region 26Ca, the facial part of the user 200 that is in contact with the overlapping region 26Ca can be cared for with more of the cosmetic composition.

The cosmetic composition in the overlapping region 26Ca then flows downward due to gravity. That is, the cosmetic composition in the overlapping region 26Ca leads to the cosmetic composition being included in greater quantity in the non-moving portion 26C that covers the space expanded by the change in shape of the space boundary portion 24C. Accordingly, the facial part of the user 200 can be cared for more effectively by the cosmetic composition through the non-moving portion 26C.

Seventh Embodiment

A seventh embodiment will be described with reference to FIG. 32, with a focus on differences from the second embodiment. Descriptions of items in common with the second embodiment will be omitted as appropriate.

As illustrated in FIG. 32, adjustment structures 22A (see FIG. 18 and the like) and adjustment structures 22C (see FIGS. 30 and 31) are formed in the nose portion 20F of the face mask 1F. Specifically, the adjustment structures 22A are mainly formed in the nasal muscle portion of the nose portion 20F, and the adjustment structures 22C are mainly formed in the portion on the outside of the nasal muscle.

Eighth Embodiment

An eight embodiment will be described with reference to FIGS. 33 through 36, with a focus on differences from the second embodiment. Descriptions of items in common with the second embodiment will be omitted as appropriate. In a nose portion 20G of a face mask 1G of the eighth embodiment, the number of adjustment structures 22A is larger than that of the face mask 1A of the second embodiment.

FIG. 34 is an enlarged schematic view illustrating the nose portion 20G, and FIG. 35 is a schematic view illustrating the nose portion 20G divided into a plurality of parts. As illustrated in FIG. 35, the adjustment structures 22A are disposed symmetrically with respect to a center line Lc. In addition, the adjustment structures 22A are not connected to the cut 6 that defines the nose portion 20G and are formed independently of the cut 6. The cut 6 changes shape relatively significantly under the influence of the difference (height difference) between the height of the nose 206 of the user 200 and the surrounding areas. On the other hand, since the adjustment structures 22A are independent of the cut (for example, the cut 6) that defines the nose portion 20G, the influence of the above difference in altitude on the adjustment structure 22A is relatively small.

As illustrated in FIG. 35, the nose portion 20G is divided into parts located in the parts A1, A2, A3, B1, B2, B3, C1, C2, and C3, with the parts A1, B1, and C1 referred to as left parts, the parts A2, B2 and C2 referred to as central portions, and the parts A3, B3 and C3 referred to as right parts. A plurality of adjustment structures 22A are formed in each of the left parts and the right parts. A plurality of adjustment structures 22A are formed in the left part and the right part so as to be separated in the vertical direction. In addition, a plurality of adjustment structures 22A are formed in the left and right parts so as to be separated in the left-right direction. That is, the plurality of adjustment structures 22A are arranged independently from each other in the vertical direction and/or the horizontal direction. As a result, in the left part and the right part, the influence of the above-mentioned relatively small difference in altitude is adjusted by the plurality of adjustment structures 22A. As a result, the change in shape of each adjustment structure 22A is small compared to the case where only a single adjustment structure 22A is formed in the left part and the right part. As a result, the nose portion of the user 200 can be more effectively cared for.

Moreover, the part located in the part C1 among the left parts is a nasal alar portion which is a part which comes into contact with a nasal ala of the user 200. Similarly, the part located in the part C3 among the right parts is a nasal alar portion which is a part which comes into contact with a nasal ala of the user 200. A plurality of adjustment structures 22A are formed in each nasal alar portion. The number of adjustment structures 22A in each nasal alar portion is two or more, preferably three or more, and more preferably four or more. In the present embodiment, the number of adjustment structures 22A in each nasal alar portion is six. The adjustment structures 22A change in shape under the influence of the difference in height between the nasal alae of the user 200 and the surrounding portion (nasal alar height difference). However, since a plurality of adjustment structures 22A are formed in each nasal alar portion, the degree of change in shape of each adjustment structure 22A is smaller than when a single adjustment structure 22A is formed for each nasal alar portion or when the adjustment structures 22A are not independent and are continuous. As a result, the nose portion of the user 200 can be more effectively cared for.

FIG. 36 is a schematic view illustrating an expanded part C1. In FIG. 36, a straight line L1 is a straight line perpendicular to a center line Lc (see FIG. 35). The line segment L2 connecting the point Q1 which is an origin point of an adjustment structure 22A and the point Q2 which is the other origin point has a different direction from the center line Lc, and also has a different direction from the straight line L1. Also, the direction Y1 of the line segment connecting the points Q1 and Q3 and the direction Y2 of the line segment connecting the points Q2 and Q3 are all different in direction from the center line Lc, and also different in direction from the straight line L1. The line segment L2 is a direction in which a force that changes the shape of an adjustment structure 22A acts when the face mask 1G is applied to the face of the user 200. With this structure, when the face mask 1G is applied to the face of the user 200, the cut (slit) connecting the point Q1 and the point Q3 and the cut connecting the point Q2 and the point Q3 spread toward both ends of the line segment L2 and the non-moving portion 26A overlaps with the lower main body portion. Due to the overlapping portion, the user's face can be more effectively cared for.

The face mask of the present invention is not limited to the above embodiments, and various modifications can be made without departing from the scope of the present invention.

REFERENCE SIGNS LIST 1, 1A, 1B, 1C, 1D, 1E, 1F, 1G Face mask
2 Base material sheet
4A, 4B Eyelid portion
6 Cut
8 Mouth portion opening
19 Forehead portion
14 Jaw portion
16A, 16B Side portion cut
20, 20A, 20B, 20C, 20D, 20E, 20F, 20G Nose portion
22, 22A, 22B, 22C Adjustment structure
24, 24A, 24B, 24C Space boundary portion
26, 26A, 26B, 26C Non-moving portion
28 Connecting portion

The invention claimed is:

1. A face mask for beauty treatment impregnated with a cosmetic composition, wherein
the face mask is configured to cover the entire face of a user, and
when a line tangent to a line segment connecting from the center of a forehead of a user with the center of a jaw of a user is given as a center line, in a nose portion which comes into contact with a nose of the user, a plurality of adjustment structures which are formed independently of each other are arranged in a portion on the left side of the center line and in a portion on the right side of the center line, respectively;
wherein the adjustment structures, which are formed independently of a cut defining the external shape of the nose portion, have
a space boundary portion, which has as origin points two points in a direction different from the direction of the center line, forming a space through a cut connecting either below or above the two points, and
a non-moving portion, which is of a same shape as the space, connected with the face mask main body at a location connecting the two points, and arranged in the space; and
are configured so that when the manner in which the face mask is applied to the face of the user is adjusted, the space boundary portion changes shape and the space expands to allow the non-moving portion to cover a region including a central portion of the space.

2. The face mask according to claim 1, wherein the plurality of adjustment structures formed independently of each other are arranged in a portion on the left side and a portion on the right side, respectively, of the center line in a nasal alar portion configured to come into contact with nasal alae of the user.

3. The face mask according to claim 2, wherein
in the nasal alar portion, a plurality of the adjustment structures are arranged in the up-down direction and/or the left-right direction independently of each other.

4. The face mask according to claim 1, wherein
the non-moving portion is configured so as to form an overlapping region which overlaps a portion of the face mask below or above the space boundary portion when the space boundary portion changes shape and expands in accordance with the shape of the nose of the user and the non-moving portion covers a region including a central portion of the space boundary portion.

\* \* \* \* \*